United States Patent [19]

Donati et al.

[11] Patent Number: 4,748,256
[45] Date of Patent: May 31, 1988

[54] PROCESS FOR THE PREPARATION OF (6-METHOXY-2-NAPHTHYL)-(1-BROMOETHYL)-KETONE AND ITS DERIVATIVES

[75] Inventors: Daniele Donati, Soave; Claudio Giordano, Vicenza; Graziano Castaldi, Briona, all of Italy

[73] Assignee: Zambon SpA, Vicenza, Italy

[21] Appl. No.: 867,954

[22] Filed: May 29, 1986

[30] Foreign Application Priority Data

May 30, 1985 [IT] Italy .............................. 20971 A/85

[51] Int. Cl.$^4$ ..................... C07D 317/16; C07C 45/00
[52] U.S. Cl. .................................. 549/453; 549/450; 568/315; 568/592
[58] Field of Search ................ 568/315, 592; 549/453, 549/450

[56] References Cited

PUBLICATIONS

Weygand/Hilgetag, Preparative Organic Chemistry, ed. Hilgetag & Martini, John Wiley & Sons, New York, 1972, pp. 62–66.

Primary Examiner—Nicky Chan
Attorney, Agent, or Firm—Cushman, Darby & Cushman

[57] ABSTRACT

A process is described for the preparation of (6-methoxy-2-naphthyl)-(1-bromoethyl)-ketone or ketals thereof (I), by selective debromination of (5-bromo-6-methoxy-2-naphthyl)-(1-bromoethyl)-ketone or ketals thereof (III) by means of a bromine acceptor in the presence of an acid and of an inert organic solvent. The bromine acceptor is preferably a phenol, a phenol ether or an aromatic ketone. The acid is preferably an halogenidric acid.

6 Claims, No Drawings

PROCESS FOR THE PREPARATION OF (6-METHOXY-2-NAPHTHYL)-(1-BROMOETHYL)-KETONE AND ITS DERIVATIVES

This invention relates to a process for preparing the compound (6-methoxy-2-naphthyl)-(1-bromoethyl)-ketone and its derivatives, and more particularly relates to the preparation of said compound or its ketals by selective debromination of (5-bromo-6-methoxy-2-naphthyl)-(1-bromoethyl)-ketone or of its ketals respectively. (6-methoxy-2-naphthyl)-(1-bromoethyl)-ketone [also known as 1-(6-methoxy-2-naphthyl)-2-bromo-propan-1-one] of formula

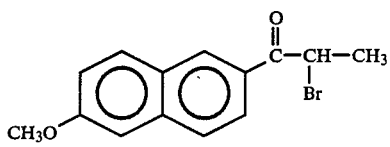

and its ketals with alcohols, glycols, glycerin, tartaric acid or derivatives (hereinafter the term "compounds I" indicates either the ketone of formula I or its derivatives) are useful intermediate in the preparation of 2-(6-methoxy-2-naphthyl)-propionic acid, of which the S(+) isomer, known as Naproxen, is a drug possessing anti-inflammatory and analgesic activity.

Some of these ketals are also useful as intermediates in the preparation of the corresponding alpha-acyloxy derivatives, which are also used in the synthesis of Naproxen.

When the compounds I undergo rearrangement by various methods, which differ according to the specific compound treated, they form 2-(6-methoxy-2-naphthyl)-propionic acid or its immediate precursors. It is important to note that the compounds I possess at least one asymmetric carbon atom, namely the carbon atom to which the bromine is bonded, and that depending on the operational method used it is possible to rearrange the suitable optically active compound I to obtain 2-(6-methoxy-2-naphthyl)-propionic acid in which the (S+) isomer predominates.

The various processes for preparing Naproxen using a compound I include those described in British Pat. No. 2.042.543 (Montedison), in European patent applications No. 34871 (Blaschim), No. 35305 (Blaschim), No. 48136 (Sagami), No. 64394 (Syntex), No. 67698 (Sagami), No. 71299 (Blaschim), No. 81993 (Syntex), No. 101124, No. 123739, No. 152004, No. 152003, No. 154853, No. 158255, No. 158913, No. 178580, all in the name of Zambon S.p.A.

According to the known art the compounds I can be prepared by bromination of (6-methoxy-2-naphthyl)-ethyl-ketone (II)

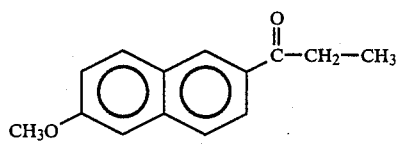

[also known as 1-(6-methoxy-2-naphthyl)-propan-1-one] or of its ketals.

The ketone of formula II and its ketals are indicated hereinafter as compounds II.

In order to obtain selective bromination on the carbon atom in the alpha position to the carbonyl, selective brominating agents such as quaternary ammonium perhalides must be used; however these have a high cost which strongly affects the final product cost, and they also present practical problems in the separation, recovery and purification of the required product.

If bromination is carried out with bromine, which is of considerably lower cost and does not present serious practical drawbacks, bromination is not selective and it results in the production of (5-bromo-6-methoxy-2-naphthyl)-(1-bromoethyl)-ketone (III)

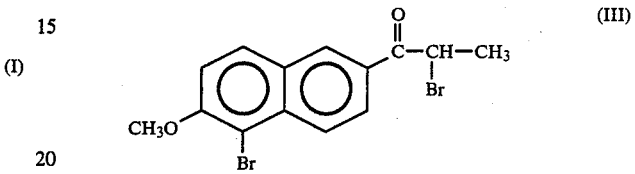

[also known as 1-(5-bromo-6-methoxy-2-naphthyl)-2-bromo-propan-1-one] or the corresponding ketals, according to the initial substance used.

The ketone of formula III and its ketals are indicated hereinafter as compounds III.

The use of compounds III in the synthesis of Naproxen implies a dehalogenation reaction in order to eliminate the bromine atom in position 5 of the naphthalenic nucleus.

The dehalogenation reaction, which can be carried out at the compound III level, but in general is carried out at the 2-(6-methoxy-2-naphthyl)-propionic acid level, i.e. after the rearrangement reaction, in all cases represents an extra stage in the process, with its consequent costs.

The requirement for a low-cost method which produces the compounds I is therefore apparent.

We have now surprisingly found that the compounds III in the presence of a suitable bromine acceptor and of a suitable acid, in inert organic solvent, lose selectively and almost quantitatively the bromine atom in position 5 of the naphthalenic nucleus, thus leading to nearly pure compounds (I) in a simple and economical manner.

Examples of acids suitable to perform the process of the invention are halogenidric acids, $HSO_3F$, $CF_3SO_3H$ or systems comprising halogenidric acids and Lewis acids, such as $HBr+ZnBr_2$ and $HCl+AlCl_3$. Examples of inert organic solvents are 1,2-dichloroethane, toluene, nitrobenzene, methylene dichloride, nitromethane and mixtures thereof. According to an embodiment of the present invention the bromine acceptor can be a compound of formula (II) which selectively bonds the bromine atom on the carbon atom in the alpha position to the carbonyl, thus also forming the corresponding compound (I).

In this case the object of the present invention is therefore a process for preparing the compounds I by reacting the corresponding compound III with a substantially equimolar quantity of the corresponding compound II in the presence of an acid.

In one of its aspects, the present invention relates to a process for preparing (6-methoxy-2-naphthyl)-(1-bromoethyl)-ketone by reacting together substantially equimolar quantities of (5-bromo-6-methoxy-2-naphthyl)-(1-bromoethyl)-ketone and (6-methoxy-2-naphthyl)-ethyl-ketone in the presence of an acid.

In another of its aspects, the present invention relates to a process for preparing ketals of (6-methoxy-2-naphthyl)-(1-bromoethyl)ketone by reacting together substantially equimolar quantities of the corresponding ketals of (5-bromo-6-methoxy-2-naphthyl)-(1-bromoethyl)-ketone and (6-methoxy-2-naphthyl)-ethyl-ketone in the presence of an acid.

As the compounds III can be easily prepared from the compounds II by bromination with bromine, a preferred aspect of this embodiment of the invention consists of a process for preparing the compounds I by reacting the corresponding compounds II with bromine, to obtain the compounds III and then reacting these with a substantially equimolar quantity of the compound II, i.e. by carrying out the following reaction sequence:

 (1)

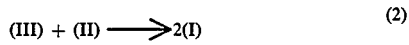 (2)

The reaction sequence 1+2 can be carried out in a single stage without isolating the intermediate III. In such a case the hydrobromic acid which is released during reaction 1 is sufficient to catalyse reaction 2.

More specifically the process for preparing compounds I from the corresponding compounds II is carried out by dissolving the predetermined quantity of compound II in a suitable inert solvent, for example 1,2-dichloroethane, and adding $Br_2$ in double the molar quantity of compound II.

Bromination is complete after a few minutes at a temperature of between 0° C. at room temperature, and analysis of the reaction mixture indicates that the compound II has been completely converted the corresponding compound III.

Without further processing the mixture, a quantity of compound II equal to the initial quantity is added.

After some hours at the same temperature the compound III has reached a degree of conversion exceeding 95%. The yield of compound I with respect to the converted compound exceeds 80%.

The compound I is isolated by conventional methods.

The final result of the process is therefore, both in stoichiometrical and practical terms, equivalent to the result which would be obtained by selective bromination of the compound II in the alpha position at the carbonyl.

While this operation could be carried out according to the known art by two alternative procedures, namely selective bromination with costly selective brominating agents or bromination with bromine followed by removal of the bromine atom in position 5 of the aromatic nucleus, by virtue of the process according to the present invention it is possible to obtain selective bromination of the compounds II in the alpha position at the carbonyl using bromine, i.e. a non-selective brominating agent, in an extremely simple and economical manner.

However the process can evidently be applied to the compounds III independently of how these have been prepared.

According to another embodiment of the present invention the selective debromination of the compounds III can be performed using other substrates able to accept the bromine atom which separates from position 5 in the aromatic nucleus of the compounds III. Examples of such bromine acceptors are aromatic compounds active to electrophilic substitution such as phenols, phenol ethers, aryl ketones, aryl-alkyl ketones, ketals of aryl-alkyl ketones and more specifically phenol, anisole, naphthols, cresols, acetophenone, benzophenone, tetrahydronaphthalene and the like. The acids suitable to perform the reaction are in any case those previously mentioned.

The following examples are given for the purpose of better illustrating the present invention, but without limiting it.

EXAMPLE 1

A solution of bromine (8.95 g; 0.056 moles) in 1,2-dichloroethane (10 ml) is added, under nitrogen at 15° C., to a solution of 1-(6-methoxy-2-naphthyl)-propan-1-one (6 g; 0.028 moles) in 1,2-dichloroethane (50 ml).

When the bromine has been completely consumed, 1-(6-methoxy-2-naphthyl)-propan-1-one (6 g; 0.028 moles) is added to the solution. The reaction mixture is kept at 15° C. for 168 hours, and is then diluted with 1,2-dichloroethane (10 ml). The solution thus obtained is washed with water and dried with sodium sulphate.

The solvent is evaporated under vacuum to yield 2-bromo-1-(6-methoxy-2-naphthyl)-propan-1-one (16.90 g; HPLC titre=78%; 0.045 moles; Yield 80%).

EXAMPLE 2

A solution of bromine (5.12 g; 0.032 moles) in 1,2-dichloroethane (10 ml) is added, under nitrogen at 15° C., to a solution of 2-ethyl-2-(6-methoxy-2-naphthyl)-4(R), 5(R)-dimethoxycarbonyl-1,3-dioxolane (6 g; 0;016 moles) in 1,2-dichloroethane (50 ml). When the bromine has been completely consumed, 2-ethyl-2-(6-methoxy-2-naphthyl)-4(R), 5(R)-dimethoxycarbonyl-1,3-dioxolane (5 g; 0.016 moles) is added. The reaction mixture is kept at 15° C. for 120 hours, and is then diluted with 1,2-dichloroethane (10 ml). The solution thus obtained is washed with water and dried with sodium sulphate.

The solvent is evaporated under vacuum to leave 2-(1-bromoethyl)-2-(6-methoxy-2-naphthyl)-4(R), 5(R)-dimethoxycarbonyl-1,3-dioxolane (14.23 g; HPLC titre=86%; 0.0270 moles; yield 84%) in diastereoisomeric mixture in which RRS:RRR=73:27 (determined by HPLC and $^1$H-NMR 200 MHz).

EXAMPLE 3

A solution of 2-ethyl-2-(6-methoxy-2-naphthyl)-1,3-dioxolane-4(R), 5(R)-dicarboxylic acid dimethylester (29.0 g, 77.5 mmol) in toluene (120 ml) and nitrobenzene (3.9 g) is cooled at −10° C., while stirring under nitrogen.

Bromine (28.5 g, 178.1 mmol) is added in 1 h under stirring to the reaction mixture. The reaction is monitored by HPLC analysis of its aliquotes. After 1 h at −10° C. the conversion of the starting material is complete and 2-(1-bromoethyl)-2-(5-bromo-6-methoxy-2-naphthyl)-1,3-dioxolane-4(R), 5(R)-dicarboxylic acid dimethylester (A) is formed in 96% yield as diastereoisomeric mixture RRS:RRR=91.5:8.5, ratio determined via HPLC analysis.

Then phenol (43.68 g, 464.7 mmol) is added as a solid all at once; the mixture is allowed to warm to +15° C. and stirred at this temperature for 3 h, then it is poured in 30 min. under vigorous stirring into a 10% aqueous solution of sodium carbonate (250 ml). The organic layer is separated and the aqueous phase is extracted with toluene (100 ml).

The combined organic extracts are washed with water, dried over sodium sulphate and the solvent is removed in vacuo.

HPLC analysis of the crude product shows that it contains essentially 2-(1-bromoethyl)-2-(6-methoxy-2-naphthyl)-1,3-dioxolane-4(R), 5(R)-dicarboxylic acid dimethylester (B) (33.35 g, 73.6 mmol, yield 95%) as a mixture of diastereoisomers RRS:RRR=91:9 [ratio determined by HPLC and $^1$H-NMR (300 MHz) analyses].

EXAMPLE 4

A solution of 2-ethyl-2-(6-methoxy-2-naphthyl)-1,3-dioxolane-4(R), 5(R)-dicarboxylic acid dimethylester (2.42 g; 6.5 mmol) in toluene (12 ml) is cooled at −10° C., while stirring under nitrogen. Bromine (2.37 g, 14.8 mmol) is added in 45 min. under stirring.

The reaction mixture is kept at −10° C. and monitored by HPLC. After 1 h at −10° C. the starting material has been completely converted and 2-(1-bromoethyl)-2-(5-bromo-6-methoxy-2-naphthyl)-1,3-dioxolane-4(R), 5(R)-dicarboxylic acid dimethylester (A) is obtained as diastereoisomeric mixture RRS:RRR=92.5:7.5, ratio determined via HPLC analysis.

Then m.cresol (4.18 g; 38.7 mmol) is added as a solid all at once. The mixture is warmed to +15° C. and stirred at this temperature for 4 h, then it is poured into a 10% aqueous sodium carbonate solution (100 ml) and extracted with dichloromethane (2×50 ml). The organic layers are washed with water (50 ml), dried over sodium sulphate and evaporated under reduced pressure.

A crude product is obtained and its HPLC analysis shows that it contains a mixture of 2-(1-bromoethyl)-2-(6-methoxy-2-naphthyl)-1,3-dioxolane-4(R), 5(R)-dicarboxylic acid dimethylester (B) (as a mixture of diastereoisomers RRS:RRR=91:9, (ratio determined via HPLC and $^1$H-NBMR (300 MHz) analyses) and of 2-(1)bromoethyl)-(5-bromo-6-methoxy-2-naphthyl)-1,3-dioxolane-4(R), 5(R)-dicarboxylic acid dimethylester (A), in ratio B:A=98:2.

EXAMPLE 5

2-(1-bromoethyl)-2-(5-bromo-6-methoxy-2-naphthyl)-1,3-dioxolane-4(R), 5(R)-dicarboxylic acid dimethylester (A) (3.45 g, 6.5 mmol) as diastereoisomeric mixture RRS:RRR=77:23, is dissolved in nitrobenzene (10 ml) saturated with hydrogen bromide at 15° C. Then phenol (7.43 g, 25.8 mmol) is added as a solid all at once and the reaction mixture is kept under stirring at +15° C. HPLC analysis shows that, 1.5 h after having added phenol, 2-(1-bromoethyl)-2-(6-methoxy-2-naphthyl)-1,3-dioxolane-4(R), 5(R)-dicarboxylic acid dimethylester (B) (diastereoisomeric mixture RRS:RRR=76:24) and 2-(1-bromoethyl)-2-(5-bromo-6-methoxy-2-naphthyl)-1,3-dioxolane-4(R), 5(R)-dicarboxylic acid dimethylester (A) (diastereoisomeric mixture RRS:RRR=77:23) are present in ratio B:A=95:5.

EXAMPLE 6

A solution of bromine (5.04 g, 31.5 mmol) in carbon tetrachloride (3 ml) is added in 5 min. to a solution of 2-ethyl-2-(6-methoxy-2-naphthyl)-1,3-dioxolane-4(R), 5(R)-dicarboxylic acid dimethylester (5.62 g, 15 mmol) in carbon tetrachloride (30 ml), while stirring at +15° C. under nitrogen.

The reaction mixture is kept at +15° C. for 1 h. An aliquote is removed and its HPLC analysis, runned after suitable work-up, shows that the conversion of the starting material is complete and 2-(1-bromoethyl)-2-(5-bromo-6-methoxy-2-naphthyl)-1,3-dioxolane-4(R), 5(R)-dicarboxylic acid dimethylester (A) is present in 98% yield as diastereosiomeric mixture RRS:RRR=91:9, ratio determined via HPLC.

Then phenol (5.64 g, 60 mmol) is added as a solid all at one once. The reaction mixture is stirred at +15° C. for 18 h, then it is poured into a 10% aqueous solution of sodium carbonate (150 ml) and extracted with dichloromethane. The combined organic layers are washed with water (100 ml), dried over sodium sulphate and the solvent is removed in vacuo.

A crude product is obtained and its HPLC analysis shows that 2-(1-bromoethyl)-2-(6-methoxy-2-naphthyl)-1,3-dioxolane-4(R), 5(R)-dicarboxylic acid dimethylester (B) and 2-(1-bromoethyl)-2-(5-bromo-6-methoxy-2-naphthyl)-1,3-dioxolane-4(R), 5(R)-dicarboxylic acid dimethylester (A) are present in ratio B:A=98:2.

EXAMPLE 7

2-(1-bromoethyl)-2-(5-bromo-6-methoxy-2-naphthyl)-5,5-dimethyl-1,3-dioxane (9.16 g, 10 mmol) is dissolved in toluene (40 ml) and nitrobenzene (2 g) saturated with HBr at room temperature. Phenol (11.28 g, 120 mmol) is added as solid; the mixture is stirred for 2.5 hours, then is poured in 30 minutes under stirring into a 10% aqueous sodium carbonate solution (150 ml), the organic layer is separated and the aqueous phase is extracted with toluene. The combined organic extracts are washed with water, dried on sodium sulphate and the solvent is removed in vacuo. 2-(1-bromoethyl)-2-(6-methoxy-2-naphthyl)-5,5-dimethyl-1,3-dioxane is obtained (75% yield).

We claim:

1. Process for the preparation of (6-methoxy-2-naphthyl)-(1-bromo-ethyl)-ketone of formula

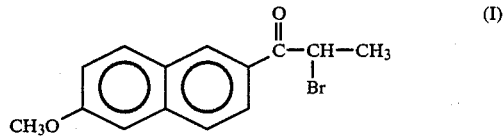

and ketals thereof, wherein (5-bromo-6-methoxy-2-naphthyl)-(1-bromo-ethyl)-ketone of the formula

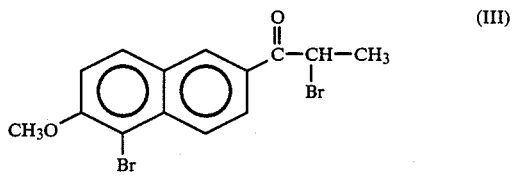

or ketal thereof are selectively debrominated by eliminating the bromine atom in the 5-position on the aromatic nucleus by means of a bromine acceptor selected from the group consisting of phenols, phenol ethers, aryl ketones, aryl-alkyl ketones and ketals of aryl-alkyl ketones and of an acid selected from the group consisting of halogenidric acids, $HSO_3F$, $CF_3SO_3H$ and systems consisting of halogenidric acids and Lewis acids, in an inert organic solvent.

2. Process according to claim 1, wherein the bromine acceptor is selected from the group consisting of phenol, naphthols, cresols and anisols.

3. Process according to claim 1, wherein the bromine acceptor is selected from the group consisting of (6-methoxy-2-naphthyl)-ethyl-ketone, acetophenone and benzophenone.

4. Process according to claim 1, wherein the acid is hydrobromic acid.

5. Process according to claim 1, wherein the inert organic solvent is selected from the group consisting of 1,2-dichloroethane, toluene, nitro-benzene, methylene dichloride, nitromethane and mixtures thereof.

6. Process according to claim 1, wherein the compound III or ketals thereof are prepared by bromination of (6-methoxy-2-naphthyl)-ethyl-ketone of the formula

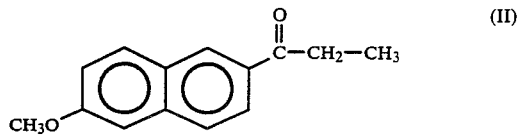

or ketals thereof, and then are directly submitted to the selective debromination reaction by adding to the reaction mixture a substantially equimolar quantity of the same starting compound (II) or ketals thereof.

* * * * *